United States Patent
Takakura

(10) Patent No.: US 7,579,591 B2
(45) Date of Patent: Aug. 25, 2009

(54) METHOD AND APPARATUS FOR ANALYZING SAMPLE

(75) Inventor: Masaru Takakura, Tokyo (JP)

(73) Assignee: Jeol Ltd., Tokyo (JP)

( * ) Notice: Subject to any disclaimer, the term of this patent is extended or adjusted under 35 U.S.C. 154(b) by 170 days.

(21) Appl. No.: 11/939,235

(22) Filed: Nov. 13, 2007

(65) Prior Publication Data

US 2008/0111072 A1    May 15, 2008

(30) Foreign Application Priority Data

Nov. 14, 2006   (JP)   ............... 2006-307592

(51) Int. Cl.
*H01J 37/26*    (2006.01)
*G01N 23/223*   (2006.01)
*G01N 23/00*    (2006.01)

(52) U.S. Cl. ............ 250/310; 250/306; 250/307; 250/492.2; 378/46

(58) Field of Classification Search .......... 250/310, 250/306, 307, 492.2; 378/46
See application file for complete search history.

(56) References Cited

U.S. PATENT DOCUMENTS 4,988,872 A * 1/1991 Nagatsuka et al. ............ 850/9
5,065,020 A * 11/1991 Kanda ............................ 850/9
2009/0052620 A1* 2/2009 Takakura ..................... 378/45

FOREIGN PATENT DOCUMENTS

JP    59-214743    4/1984
JP    63-313043    12/1988

* cited by examiner

*Primary Examiner*—Nikita Wells
(74) *Attorney, Agent, or Firm*—The Webb Law Firm

(57) ABSTRACT

Method and apparatus for performing sample analysis using both the WDS and an energy-dispersive X-ray spectrometer (EDS). The analysis starts with irradiating the sample with an electron beam. Characteristic X-rays emanating from the sample are spectrally dispersed and detected by the WDS. The intensities of the characteristic X-rays at positions where the characteristic X-ray peaks are detected are measured. At this time, the background intensities of the characteristic X-rays at the positions where the characteristic X-ray peaks are detected are found based on a mean atomic number calculated using values which are derived by quantitative analysis based on the characteristic X-ray intensities measured by the EDS at the corresponding analysis positions on the sample. The background intensities are subtracted from the peak intensities at the positions where the characteristic X-ray peaks are detected by the WDS. Thus, the net characteristic X-ray intensities are found.

5 Claims, 6 Drawing Sheets

METHOD AND APPARATUS FOR ANALYZING SAMPLE

BACKGROUND OF THE INVENTION

1. Field of the Invention

The present invention relates to method and apparatus for analyzing a sample by irradiating the sample with an electron beam, spectrally dispersing and detecting the characteristic X-rays emanating from the sample in response to the irradiation by a wavelength-dispersive X-ray spectrometer, and measuring the intensities of the characteristic X-rays at the positions where characteristic X-ray peaks are detected.

2. Description of Related Art

In a sample analyzer having the structure of an electron probe microanalyzer (EPMA), a focused electron beam, or an electron probe, is directed at a sample, and characteristic X-rays emanating from the sample by the irradiation are spectrally dispersed and detected by a wavelength-dispersive X-ray spectrometer (WDS). The intensities of characteristic X-rays at the positions where characteristic X-ray peaks are detected are measured. Based on the results of the measurements of the characteristic X-ray intensities, qualitative analysis can be performed at the analysis position on the sample.

One example of peak profile of characteristic X-rays spectrally dispersed by a wavelength-dispersive X-ray spectrometer is shown in FIG. 1, where a characteristic X-ray peak A is shown. The peak intensity detected at the characteristic X-ray peak A is Ip. The peak intensity Ip includes background intensity Ib at the position of the peak A. A value In obtained by subtracting the background intensity Ib from the peak intensity Ip is the net characteristic X-ray intensity at the peak A.

Accordingly, when quantitative analysis of a sample is made using characteristic X-rays spectrally dispersed by a wavelength-dispersive X-ray spectrometer, the following operations need to be performed. The background intensity at the position where a characteristic X-ray peak is detected is found. The background intensity is subtracted from the detected peak intensity, thus calculating the net characteristic X-ray intensity. Quantitative analysis is made based on the characteristic X-ray intensity.

In this case, it is impossible in principle to directly detect only the background intensity Ib at the characteristic X-ray peak A. Therefore, the average value of the background intensity BL at a background position on the shorter wavelength side of the position of the peak A and the background intensity BH at a background position on the longer wavelength side is calculated. The net characteristic X-ray intensity In is found based on the above-described method while taking the average value as the background intensity Ib at the peak position.

Another conceivable method disclosed in Japanese Patent Laid-Open No. S63-313043 consists of estimating background by finding the relationship between the mean atomic number and the background from plural reference samples, measuring only peak intensities during measurement of unknown samples, and finding the mean atomic number from the measured values during calculations for quantitative corrections.

A sample analyzer can consist of an electron probe microanalyzer equipped with a wavelength-dispersive X-ray spectrometer (WDS) and also with an energy-dispersive X-ray analyzer (EDS). In a method being discussed (see Japanese Patent Laid-Open No. S59-214743), each value counted by the EDS is multiplied by a constant coefficient. The resulting product is used as the background component of the characteristic X-ray peak derived by the WDS.

In order to measure the peak intensities of characteristic X-rays spectrally dispersed by a wavelength-dispersive X-ray spectrometer and to measure background intensities at background positions respectively on the shorter and longer wavelength sides of the peak detection position, it is necessary to move an analyzing crystal into the background positions on the shorter wavelength side and on the longer wavelength side, respectively. Consequently, there is the problem that the time taken to move the analyzing crystal prolongs the measurement time.

Especially, when measurements are made at multiple analysis positions within a given region on a sample, it is necessary to move the analyzing crystal as described above into each analysis position. Therefore, a much longer measurement time is required as compared with the case in which only peak intensities are measured.

A sample analyzer equipped with a wavelength-dispersive X-ray spectrometer and an energy-dispersive X-ray spectrometer suffers from a similar problem. The analyzer described in the above-cited Japanese Patent Laid-Open No. S59-214743 is designed to solve this problem.

SUMMARY OF THE INVENTION

It is an object of the present invention to provide a method and apparatus for analyzing a sample using a wavelength-dispersive X-ray spectrometer (WDS) and an energy-dispersive X-ray spectrometer (EDS) in such a way that analysis of the sample using the WDS is performed efficiently.

A first method of analyzing a sample in accordance with the present invention consists of irradiating the sample with an electron beam, spectrally dispersing and detecting characteristic X-rays emanating from the sample in response to the irradiation by a wavelength-dispersive X-ray spectrometer (WDS), and measuring the intensities of the characteristic X-rays at positions where characteristic X-ray peaks are detected. In this method of sample analysis, the background intensities of the characteristic X-rays at the positions where the characteristic X-ray peaks are detected are found based on a mean atomic number calculated using values derived by quantitative analysis based on the intensities of the characteristic X-rays measured by an energy-dispersive X-ray spectrometer (EDS) at corresponding analysis positions on the sample. The background intensities are subtracted from the peak intensities at the positions where the characteristic X-ray peaks are detected by the WDS, thus finding the net characteristic X-ray intensities.

A second method of analyzing a sample in accordance with the present invention includes the steps of: irradiating the sample with an electron beam; spectrally dispersing and detecting characteristic X-rays emanating from the sample in response to the irradiation by a wavelength-dispersive X-ray spectrometer (WDS); finding the background intensities of the characteristic X-rays at positions where characteristic X-ray peaks were detected in the previous detecting step based on a mean atomic number calculated using values derived by quantitative analysis based on characteristic X-ray intensities measured by an energy-dispersive X-ray spectrometer (EDS) at corresponding analysis positions on the sample; and subtracting the background intensities from the peak intensities at the characteristic X-ray peak positions detected by the WDS to thereby find the net characteristic X-ray intensities.

An apparatus for analyzing a sample in accordance with the present invention has: irradiation device for irradiating the sample with an electron beam; detection device for spectrally dispersing and detecting characteristic X-rays emanating from the sample in response to the irradiation by a wavelength-dispersive X-ray spectrometer (WDS); computing device for finding the background intensities of the characteristic X-rays at positions where characteristic X-ray peaks are detected by the detection device based on a mean atomic number calculated using values derived by quantitative analysis based on characteristic X-ray intensities measured by an energy-dispersive X-ray spectrometer (EDS) at corresponding analysis positions on the sample; and computational device for subtracting the background intensities from the peak intensities at the characteristic X-ray peak positions detected by the WDS to thereby find the net characteristic X-ray intensities.

In the present invention, the background intensities at the peak detection positions of the characteristic X-rays spectrally dispersed by the WDS are found based on the mean atomic number calculated using the values derived by quantitative analysis based on the characteristic X-ray intensities that have been measured by the EDS at the corresponding analysis positions on the sample. The net characteristic X-ray intensities are calculated by subtracting the background intensities from the peak intensities at the positions where the characteristic X-ray peaks are detected by the WDS.

Consequently, the background intensities at the peak detection positions can be found without measuring either background intensities at positions on the shorter wavelength side of the peak detection positions of the characteristic X-rays spectrally dispersed by the WDS or background intensities at positions on the longer wavelength side. As a result, samples can be analyzed efficiently with the WDS.

Other objects and features of the invention will appear in the course of the description thereof, which follows.

DESCRIPTION OF THE PREFERRED EMBODIMENTS

Figure 1:
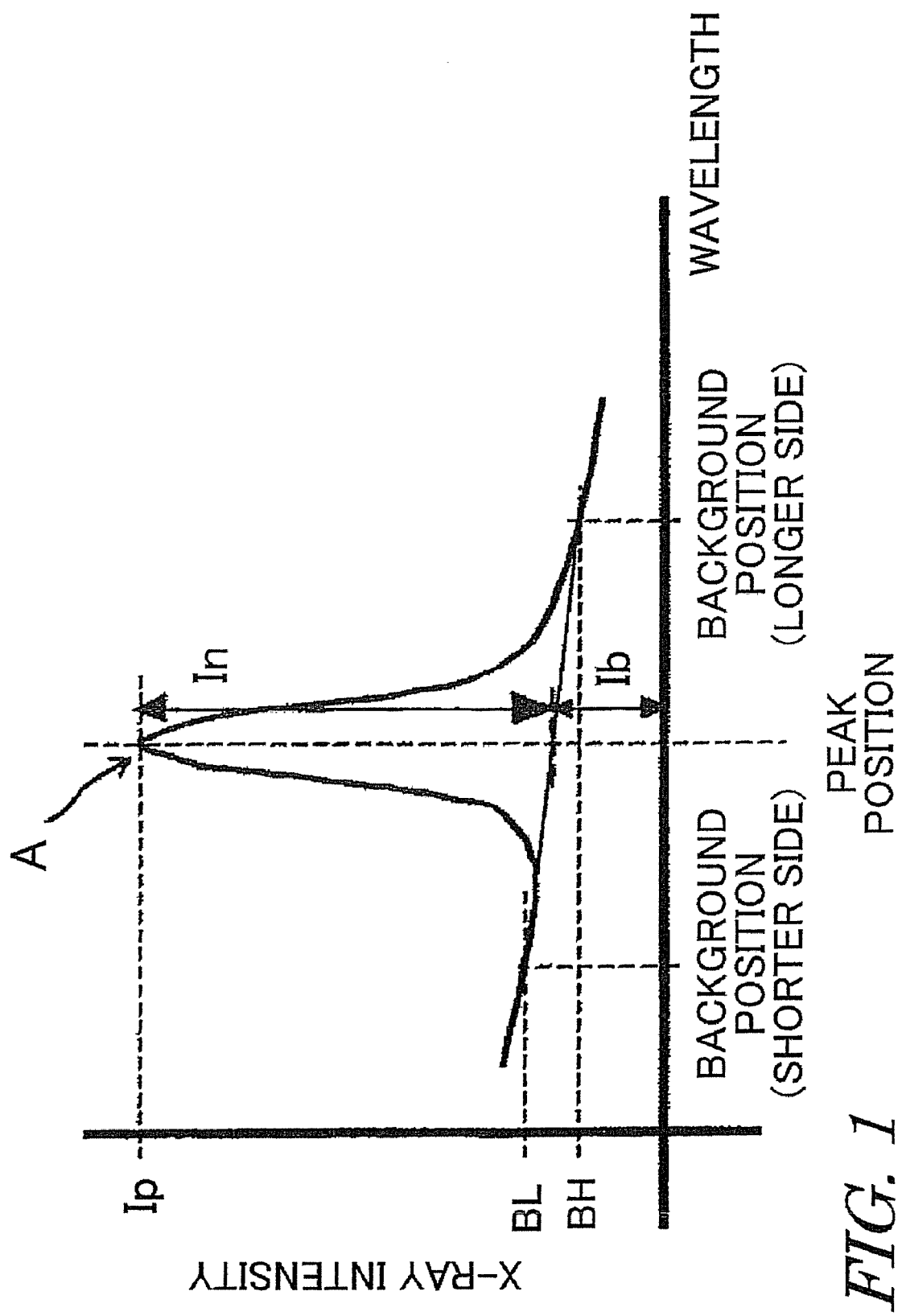
FIG. 1 is a graph showing one example of a peak profile of characteristic X-rays spectrally dispersed by a wavelength-dispersive X-ray spectrometer.
Figure 2:
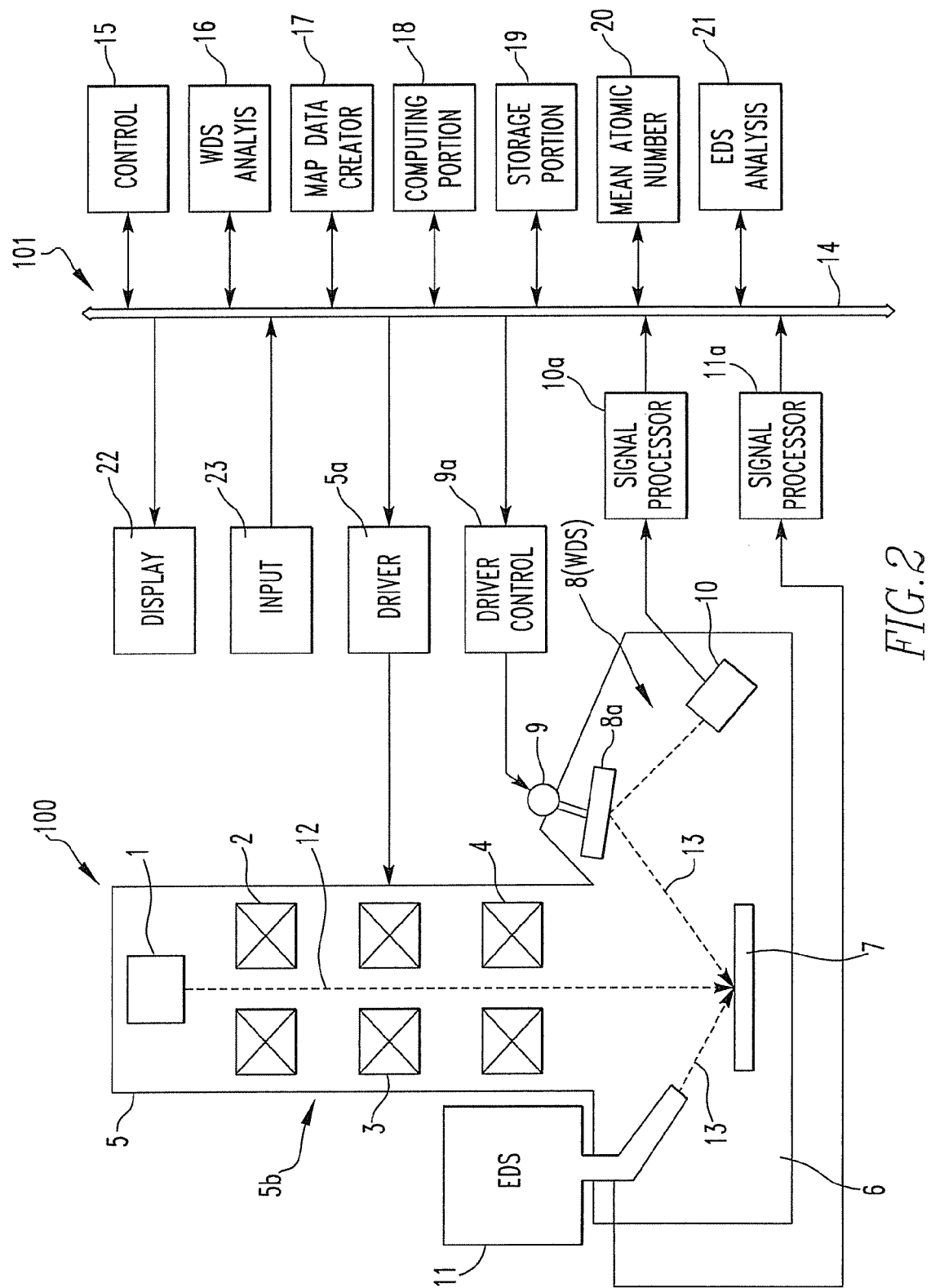
FIG. 2 is a schematic block diagram of a sample analysis apparatus according to one embodiment of the present invention.
Figure 3:
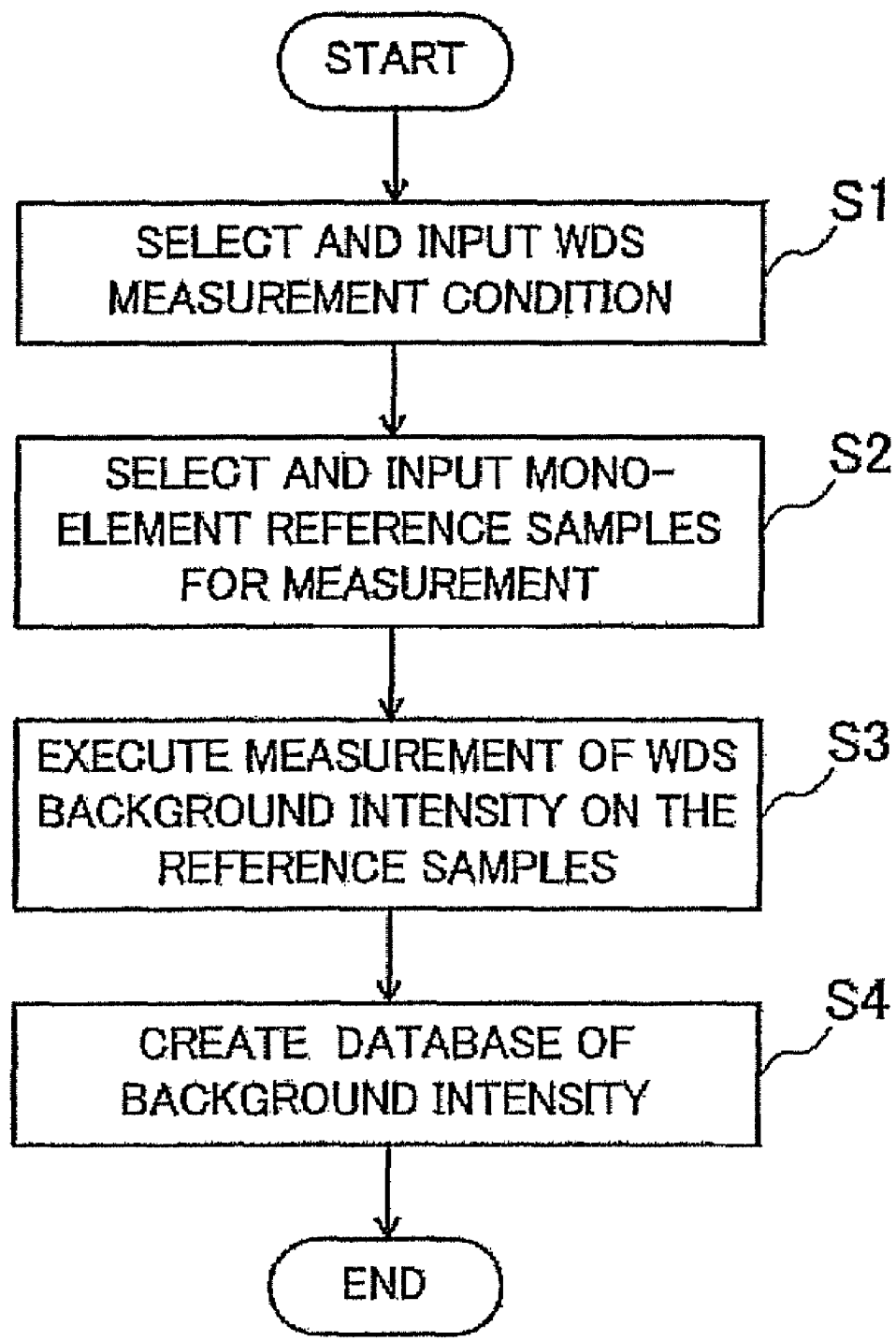
FIG. 3 is a flowchart illustrating a method of creating WDS background data.

The present invention is hereinafter described in detail with reference to the accompanying drawings. FIG. 2 is a schematic diagram of a sample analysis apparatus according to one embodiment of the present invention. The apparatus has an apparatus body 100 and a control system 101.

The apparatus body 100 includes an electron optical column 5 in which an electron gun 1 is disposed. An electron beam 12 is emitted from the gun 1 and accelerated at a given accelerating voltage toward a sample 7. The beam 12 emitted from the gun 1 is sharply focused onto the sample 7 by lens action produced by a condenser lens 2 and an objective lens 4.

As a result, an electron probe consisting of the focused electron beam 12 hits the sample 7.

If necessary, the beam 12 is deflected by a deflector 3 and made to hit a specified analysis location (analysis position) on the sample 7. The electron gun 1, condenser lens 2, deflector 3, and objective lens 4 together constitute an electron optical system 5b.

Characteristic X-rays 13 are produced from the analysis position on the sample 7 hit by the electron beam 12 in this way. The characteristic X-rays 13 are spectrally dispersed and detected by wavelength-dispersive X-ray spectrometers (WDS) 8 (only one is shown), each made up of a set of analyzing crystals 8a, a driver mechanism 9 for driving the analyzing crystals, and an X-ray detector 10.

In the single WDS 8, there are plural kinds of analyzing crystals 8a for the single X-ray detector 10. The plural wavelength-dispersive X-ray spectrometers (WDS) 8 are equipped in a sample chamber 6. Thus, a multichannel instrument is built. One WDS forms one channel.

An output signal based on detected characteristic X-rays 13 is output to a signal processor 10a from the X-ray detector 10. In the signal processor 10a, a detection signal based on the output signal is output as digital data to a bus line 14.

The characteristic X-rays 13 produced from the sample 7 as described previously are spectrally dispersed and detected by an energy-dispersive X-ray spectrometer (EDS) 11.

The EDS 11 produces an output signal based on the detected characteristic X-rays 13 to another signal processor 11a. The signal processor 11a outputs a detection signal based on the output signal as digital data to the bus line 14.

The sample 7, analyzing crystals 8a, and X-ray detector 10 are placed within the sample chamber 6. The inside of the sample chamber 6 and electron optical column 5 is evacuated to a vacuum by a vacuum pumping system (not shown). The sample 7 is placed on a sample stage (not shown) within the sample chamber 6.

As the sample 7 is irradiated with the electron beam 12, electrons to be detected, such as secondary electrons produced from the sample 7, are detected by an electron detector (not shown) mounted within the sample chamber 6. The control system 101 creates an image of the sample based on the results of detection of the electrons made by the detector and displays the image on its display portion 22.

An optical microscope (not shown) is disposed in the apparatus body 100. It is possible to obtain an optical image of the sample by the optical microscope. The optical image derived in this way is displayed on the display portion 22.

The electron optical system 5b mounted in the electron optical column 5 is driven by a driver mechanism 5a. The driver mechanism 9 for driving the analyzing crystals is mounted in the sample chamber 6 and has a driver source consisting, for example, of a motor. The driver mechanism 9 is driven by a driver control 9a. Drive signals are supplied from a control portion 15 to the driver mechanism 5a and drive control 9a via the bus line 14. Consequently, the electron optical system 5b and crystal-driving mechanism 9 are controllably driven by the control portion 15.

Also connected with the bus line 14 are a WDS quantitative analysis portion 16, a map data creation portion 17, a computing portion 18, a data storage portion 19, a mean atomic number-calculating portion 20, an EDS quantitative analysis portion 21, and the display portion 22. These components are controlled by the control portion 15. The operations of the components will be described later. The control portion 15 has an internal storage area having a given storage capacity.

An input portion 23 is also connected with the bus line 14. The input portion 23 includes a pointing device (such as a computer mouse) and a keyboard. The operator can perform manual manipulations to drive the analyzing crystals or to move the sample stage by manipulating the input portion 23. Manipulation signals produced in this way are sent to the control portion 15 via the bus line 14.

The sample stage on which the sample 7 is placed is driven by a stage-moving mechanism (not shown), which is controllably driven by the control portion 15.

The driver mechanisms 5a, driver control 9a, signal processors 10a, 11a, bus line 14, control portion 15, WDS quantitative analysis portion 16, map data creation portion 17, computing portion 18, data storage portion 19, mean atomic number-calculating portion 20, EDS quantitative analysis portion 21, display portion 22, input portion 23 shown in FIG. 2, and other components together form the control system 101.

The sample analysis apparatus according to one embodiment of the present invention is constructed as described so far. A method of sample analysis according to an embodiment of the present invention is next described by referring also to FIGS. 3-6.

In the present invention, a database of WDS background data is previously created. A method of creating the database is described now by referring to FIGS. 2 and 3. There are plural WDS units in the sample chamber 6 of the apparatus body 100. It is necessary to acquire a different set of data for each different analyzing crystal and for each different species of characteristic X-rays for each different WDS unit. Then, a corresponding database of WDS background data needs to be created and stored in the storage portion 19.

First, plural kinds of reference samples having known mean atomic numbers are placed in the sample chamber 6. Mono-element samples can be used as the reference samples. In the present embodiment, a reference sample made of Si (silicon) having an atomic number of 14, a reference sample made of Ti (titanium) having an atomic number of 22, a reference sample made of Fe (iron) having an atomic number of 26, a reference sample made of Cu (copper) having an atomic number of 29, a reference sample made of Mo (molybdenum) having an atomic number of 42, a reference sample made of Cd (cadmium) having an atomic number of 48, and a reference sample made of Au (gold) having an atomic number of 79 are prepared. These reference samples are placed on the sample stage.

In addition to such mono-element reference samples, samples made of compounds or alloys having known compositions may be used as the reference samples. If the composition of the used reference sample is known, the mean atomic number of the sample can be determined.

The reference samples (reference elements) are placed at different locations on the sample stage. These locations of the reference samples on the stage are stored in the data storage portion 19. Under this condition, WDS measurement conditions are selected and entered via the input portion 23. For example, one measurement condition is the accelerating voltage of the electron beam 12 emitted from the electron gun 1. For instance, 10 kV, 15 kV, 20 kV, 25 kV, and 30 kV are selected as five conditions, i.e., five values of the accelerating voltage of the electron beam 12, and entered. The measurement conditions are temporarily stored in the storage area of the control portion 15 from the input portion 23 (step S1).

The operating conditions (e.g., the operating conditions of the electron gun 1 and operating conditions of the various lenses) for the electron optical system 5b corresponding to these values of the accelerating voltage are previously stored in the data storage portion 19.

Then, which of the reference samples on the sample stage to be used are determined and inputs are made via the input portion 23. In the present embodiment, the reference samples of Si, Ti, Fe, Cu, Mo, Cd, and Au are used. These reference samples are selected, and corresponding inputs are made. Information about the inputs is temporarily stored in the storage area of the control portion 15 from the input portion 23 (step S2).

Then, the WDS background intensities of the reference samples selected as described above are measured (step S3), and a database is created (step S4).

That is, the sample stage is moved under control of the control portion 15. The reference sample of Si is moved into a location on the sample stage hit by the electron beam 12. The motion of the sample stage is carried out based on the position of the reference sample of Si on the stage stored in the data storage portion 19.

Under this condition, the electron beam 12 accelerated by an accelerating voltage of 10 kV under control of the control portion 15 is made to impinge on the reference sample through the electron optical system 5b. The irradiated reference sample produces characteristic X-rays.

At this time, the analyzing crystal 8a is moved by the driver mechanism 9 to bring the crystal into a position where characteristic X-ray peaks produced from the first element are detected, the first element being included in the elements i to be analyzed by a surface analysis measurement as described later.

Under this condition, the X-ray intensities are measured via the X-ray detector 10 and signal processor 10a. The measured X-ray intensities are stored as background intensities in the data storage portion 19, the background intensities being included in the characteristic X-ray peaks arising from the first element detected at the sample analysis point (analysis location) given by a mean atomic number of 14 (corresponding to the atomic number of Si) when the accelerating voltage of the electron beam 12 is 10 kV.

Then, the sample stage is moved under control of the control portion 15 to bring the reference sample of Ti on the sample stage into the position where it is hit by the electron beam 12. The motion of the sample stage is carried out based on the position of the reference sample of Ti on the sample stage, the position being stored in the data storage portion 19.

Under this condition, the electron beam 12 accelerated at the accelerating voltage of 10 kV is made to hit the reference sample by the electron optical system 5b under control of the control portion 15. The reference sample irradiated with the beam 12 produces characteristic X-rays.

At this time, the analyzing crystal 8a is placed in the position where the characteristic X-ray peaks arising from the first element are detected in the same way as the foregoing.

Under this condition, the X-ray intensities are measured via the X-ray detector 10 and signal processor 10a. The measured X-ray intensities are stored as background intensities in the data storage portion 19, the background intensities being included in the characteristic X-ray peaks arising from the first element and detected at the sample analysis point indicated by the mean atomic number of 22 (corresponding to the atomic number of Ti) when the accelerating voltage of the electron beam 12 is 10 kV.

Subsequently, the X-ray intensities are measured on the reference samples of Fe, Cu, Mo, Cd, and Au in the same way as in the above-described measurement. The measured X-ray intensities are stored as background intensities in the data storage portion 19, the background intensities being included in the characteristic X-ray peaks arising from the first element and measured at the sample analysis points respectively indicated by the mean atomic numbers of 26 (corresponding to the atomic number of Fe), 29 (corresponding to the atomic number of Cu), 42 (corresponding to the atomic number of Mo), 48 (corresponding to the atomic number of Cd), and 79 (corresponding to the atomic number of Au) when the accelerating voltage of the electron beam 12 is 10 kV. After these operations, the beam irradiation is once stopped.

Then, the sample stage is moved under control of the control portion 15 to again bring the reference sample of Si on the stage into the position where the sample is irradiated with the electron beam 12.

Furthermore, the analyzing crystal is moved by the driver mechanism 9 to bring the analyzing crystal 8*a* into the position where the characteristic X-ray peaks arising from the second element are detected, the second element being included in the elements i to be analyzed during the surface analysis measurement. Then, the reference sample is irradiated with the electron beam 12 at the accelerating voltage of 10 kV in the same way as in the above-described measurement.

Under this condition, the X-ray intensities are measured via the X-ray detector 10 and signal processor 10*a*. The measured X-ray intensities are stored as background intensities in the data storage portion 19, the background intensities being included in the characteristic X-ray peaks arising from the second element and measured at the sample analysis point indicated by the mean atomic number of 14 when the accelerating voltage of the electron beam 12 is 10 kV.

Subsequently, similar operations are performed for the reference samples of Ti, Fe, Cu, Mo, Cd, and Au, and their X-ray intensities are measured. The measured X-ray intensities are stored as background intensities in the data storage portion 19, the background intensities being included in the characteristic X-ray peaks which arise from the second element and which are measured at the sample analysis points indicated by the mean atomic numbers of 22, 26, 29, 42, 48, and 79 when the accelerating voltage of the beam 12 is 10 kV. After these operations, the beam irradiation is once stopped.

Thereafter, the analyzing crystals 8*a* are successively placed into the positions where the characteristic X-ray peaks arising from the third, fourth, and following elements of the elements i to be analyzed during the surface analysis measurement are detected. The X-ray intensities are measured for the reference samples of Si, Ti, Fe, Cu, Mo, Cd, and Au. In this way, background intensities included in the characteristic X-ray peaks are derived, the X-ray peaks being emitted from the third, fourth, and following elements measured at the sample analysis points indicated by the mean atomic numbers of 14, 22, 26, 29, 42, 48, and 79 when the accelerating voltage of the electron beam 12 is 10 kV. Data about the derived intensities is stored in the data storage portion 19. The process described so far is carried out when the accelerating voltage of the electron beam 12 is set to 10 kV.

When the background intensities included in the characteristic X-ray peaks emitted from the first, second, and following elements are derived, if the element constituting any reference sample is coincident with the nth element (i.e., the atomic number of the element constituting the reference sample is coincident with the atomic number of the nth element), the measurement of the X-ray intensities emitted from the nth element using the analyzing crystal 8*a* is skipped. The process goes to the measurement of the X-ray intensities of the next (n+1)th element while using the reference sample. The X-ray intensity measured, using the reference sample, under the condition where the analyzing crystal 8*a* is placed in the characteristic X-ray peak position of the nth element corresponds to the characteristic X-ray peak produced from the nth element. The background intensities that the user wants to obtain cannot be measured.

The accelerating voltage of the electron beam 12 is set to 15 kV, 20 kV, 25 kV, and 30 kV, in turn. The above-described process is repeated but at these accelerating voltage settings. After these operations, the electron beam irradiation is stopped.

In this way, the X-ray intensities at the characteristic peak positions arising from the first, second, and following elements and measured at the sample analysis points indicated by the mean atomic numbers of 14, 22, 26, 29, 42, 48, and 79 are obtained when the accelerating voltage of the beam 12 is 10 kV, 15 kV, 20 kV, 25 kV, and 30 kV. Sets of data derived are stored as a database in the data storage portion 19.

The database stored in the data storage portion 19 assumes the form of a table of data items. A mathematical formula (approximate formula) indicating an approximate curve may be found by the computing portion 18, and the mathematical formula may be stored as a database in the data storage portion 19.

Figure 6:
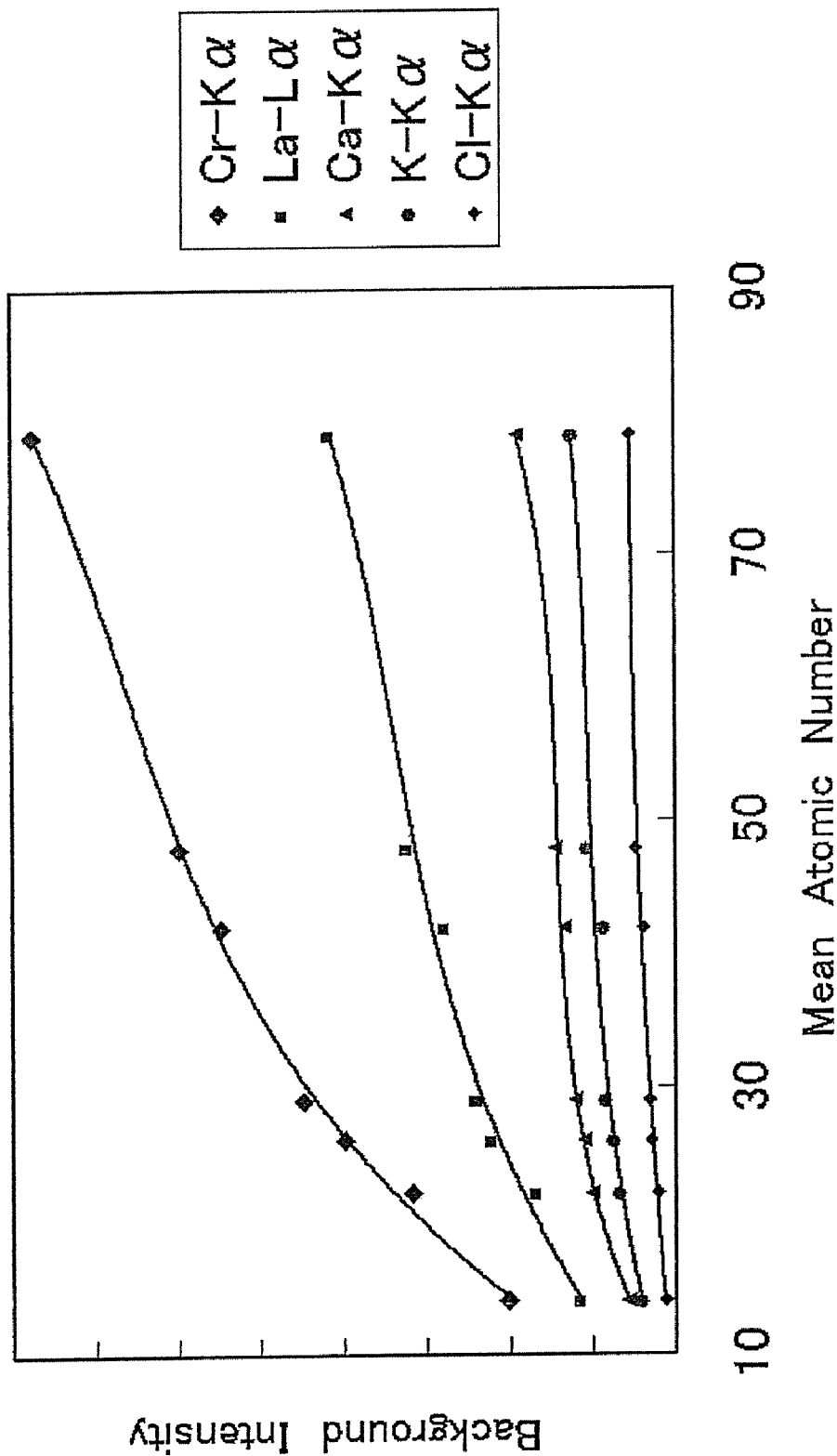
FIG. 6 is a graph illustrating a database of background intensities.

One example of the database is described by referring to FIG. 6, which is a graph where background intensities corresponding to mean atomic numbers are represented as approximate curves when the accelerating voltage of the electron beam is 20 kV.

In the graph of FIG. 6, examples of the elements i to be analyzed during the surface analysis measurement include Cr, La, Ca, K, and Cl. Cr-Kα, La-Lα, Ca-Kα, K-Kα, and Cl-Kα indicate the characteristic X-ray species of the various elements.

Spectral positions at which the characteristic X-ray peaks are detected using the analyzing crystals 8*a* are determined for the individual characteristic X-ray species. In the above-described process for measuring the X-ray intensities, the analyzing crystals 8*a* are successively placed into these characteristic X-ray peak detection positions corresponding to the characteristic X-ray species.

In this way, a database of background intensities corresponding to arbitrary mean atomic numbers at the beam accelerating voltages of 10 kV, 15 kV, 20 kV, 25 kV, and 30 kV is obtained from data about the X-ray intensities at the characteristic X-ray peak positions of the first, second, and following elements measured at the sample analysis points indicated by the mean atomic numbers of 14, 22, 26, 29, 42, 48, and 79 when the beam accelerating voltage is set to 10 kV, 15 kV, 20 kV, 25 kV, and 30 kV. The database is stored in the data storage portion 19.

After execution of the creation of the WDS background database, samples to be analyzed by a surface analysis technique are measured. This measurement using the surface analysis technique is described by referring to FIGS. 2, 4, and 5.

In the surface analysis measurement, the sample 7 to be analyzed is placed within the sample chamber 6 of the apparatus body 100. The sample 7 is placed on the sample stage within the sample chamber 6.

Figure 4:
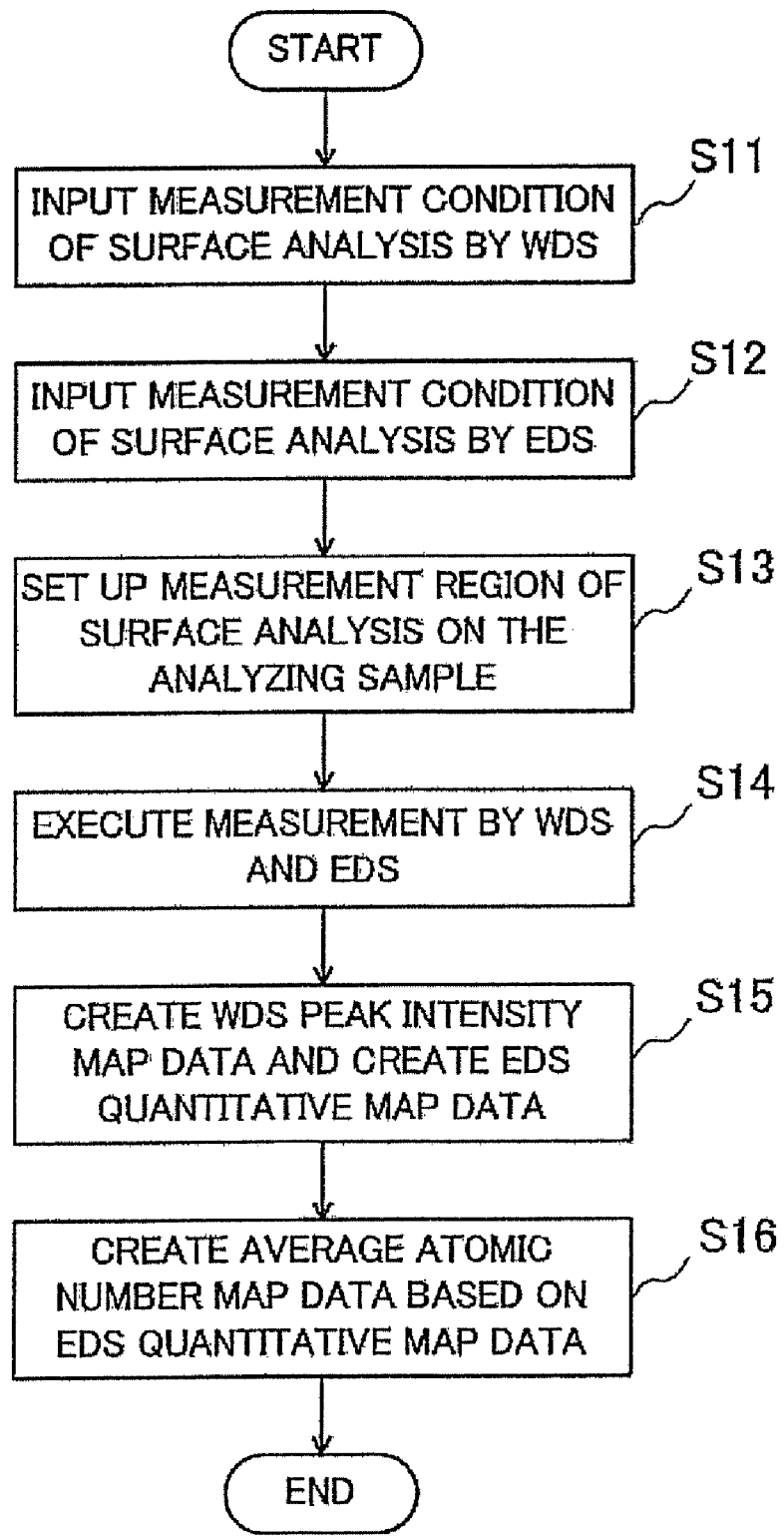
FIG. 4 is a flowchart illustrating a preliminary process for surface analysis measurement using WDS.

The preliminary process illustrated in FIG. 4 is first carried out. The operator manipulates the input portion 23 to enter conditions under which surface analysis measurements are made by WDS. In the present embodiment, the accelerating voltage of the electron beam 12 is selected and entered. For example, an accelerating voltage of 20 kV is entered as a surface analysis condition (step S11).

Furthermore, conditions under which surface analysis measurements are made by EDS are entered. In the present embodiment, WDS measurement and EDS measurement are performed at the same time. Therefore, the measurement condition (20 kV in this example) common to both kinds of measurement is set (step S12).

The sample 7 is irradiated with the electron beam 12 under the above-described condition. Electrons, such as secondary electrons, to be detected are produced from the sample 7 in response to the irradiation. The electrons are detected by an electron detector (not shown). The control system 101 creates a sample image based on the detection. The image is displayed on the display portion 22. The operator manipulates the input portion 23 while visually checking the sample image displayed on the display portion 22. In this way, a measurement region (analyzed region) is set on the sample 7 (step S13).

The step S13 may also be carried out based on an optical image of the sample 7.

Then, simultaneous WDS/EDS measurement is carried out. That is, given plural measurement positions (analysis points) in the measurement region on the sample 7 are successively irradiated with the electron beam 12. Characteristic X-rays 13 produced from the measurement positions are detected by the WDS 8 and EDS 11 (step S14).

The output signal from the WDS 8 indicative of detected characteristic X-rays 13 is sent to the bus line 14 through the signal processor 10a. The map data creation portion 17 connected with the bus line 14 creates map data about WDS peak intensities based on the output signal from the WDS 8. The map data is stored in the data storage portion 19. The peak intensities included in the map data include background intensities. The background intensities are added to the net characteristic X-ray intensities.

The output signal from the EDS 11 indicative of detected characteristic X-rays 13 is sent to the bus line 14 through the signal processor 11a. The EDS quantitative analysis portion 21 connected with the bus line 14 creates spectral map data based on the output signal from the EDS 11 and performs quantitative or semi-quantitative analysis to create quantitative map data based on values derived from main constituent components by quantitative analysis. The quantitative map data consists of the values derived by the quantitative analysis and is stored in the data storage portion 19 (step S15).

Then, map data about mean atomic numbers is created based on the results of EDS measurements (step S16).

That is, the items of the quantitative map data are read out from the data storage portion 19 for each data item about the values derived by the quantitative analysis, and are sent to the mean atomic number-calculating portion 20. The mean atomic number-calculating portion 20 calculates the mean atomic number at each measurement position within the measurement region based on the data. The calculation is carried out as follows.

Let $Z_A$, $Z_B$, $Z_C$, ... be the atomic numbers of the elements A, B, C, ... measured by EDS. Let $C_A$, $C_B$, $C_C$, ... be the normalized mass concentrations of the elements. The mean atomic number Z (x, y) at a measurement position (x, y) is calculated using the following equation.

$$Z(x,y)=\Sigma(C_t Z_t)(t=A, B, C, ...)$$

The mean atomic number-calculating portion 20 calculates the mean atomic number at each measurement position using the above-described formula. Data about the mean atomic number calculated in a corresponding manner to each measurement position is sent to the map data creation portion 17, which creates mean atomic number map data. The process executed in step S16 is carried out as described so far.

Figure 5:
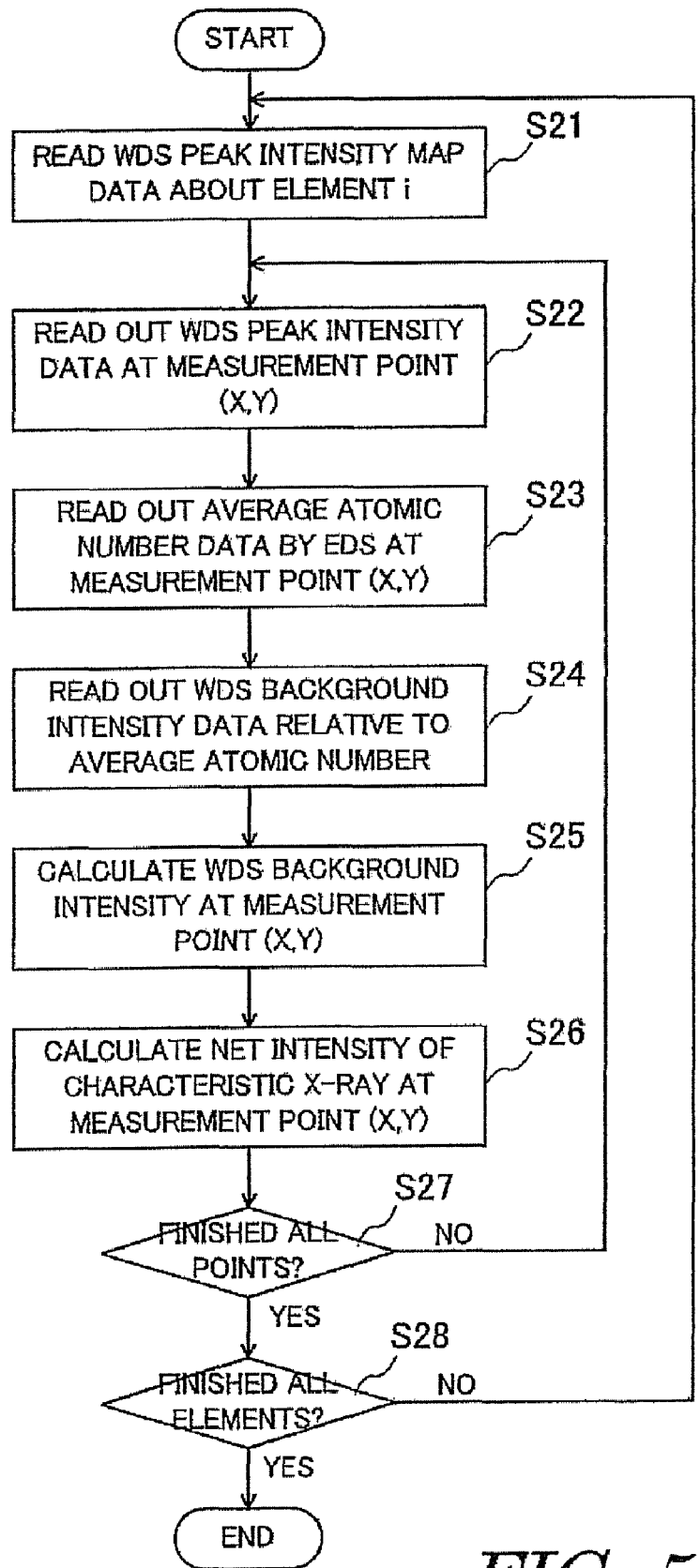
FIG. 5 is a flowchart illustrating a post process for surface analysis measurement using WDS.

Subsequently to the preliminary process, a post process illustrated in FIG. 5 is performed.

WDS peak intensity map data which has been derived by the preliminary process and which is about the element i to be analyzed is read from the data storage portion 19 (step S21) under control of the control portion 15. WDS peak intensity data which has been derived by the preliminary process and which is about the measurement position (x, y) within the measurement region is read out (step S22).

Mean atomic number data derived by EDS analysis data about each corresponding measurement position (x, y) is read from the data storage portion 19 (step S23).

The database of the background intensities stored in the data storage portion 19 is read out, the database having been created in the step S4. In this case, when analysis is performed in the present embodiment, the electron beam accelerating voltage is 20 kV and so the database of the background intensities relative to the mean atomic numbers when the accelerating voltage is 20 kV is read out (step S24).

The sets of data read out in the steps S22, S23, and S24 are sent to the computing portion 18. The computing portion 18 finds the WDS background intensities about the element i based on the mean atomic number data read out in the step S23 and on the database of the background intensities read out in the step S24. The background intensities are found from the relationship between the mean atomic number included in the data about the characteristic X-ray species corresponding to the element i and the background intensity (step S25).

Furthermore, the computing portion 18 subtracts the WDS background intensity found as described above from the WDS peak intensity read out in the step S22 to calculate the net WDS characteristic X-ray intensity (step S26).

The steps S22-S26 are carried out at every measurement position (x, y) in the measurement region (step S27). The steps are performed for all the elements to be analyzed (step S28).

Consequently, the net characteristic X-ray intensity can be found for each of all the elements to be analyzed at every measurement position (x, y) in the measurement region on the sample 7.

Data about the net intensities is sent to the map data creation portion 17 to create map data about the net intensities. The created map data is sent to the WDS quantitative analysis portion 16, where well-known quantitative analysis (such as ZAF quantitative correction procedure) is performed. The results of the quantitative analysis are displayed on the display portion 22.

In the above embodiment, the electron beam-accelerating voltage is set to 20 kV. The accelerating voltage may also be set to 10 kV, 15 kV, 25 kV, or 30 kV. In this case, the accelerating voltage set in steps S11 and S12 is the used accelerating voltage. The WDS background intensity data (i.e., the database of the background intensities) read out in the step S24 may be so varied as to correspond to the accelerating voltage.

Where values of accelerating voltage (e.g., 12 kV and 17 kV) between the above-described values of accelerating voltage are used, corresponding background intensities can be found by interpolation of the above-described data.

In this way, a method of analyzing a sample in accordance with the present invention starts with irradiating the sample with an electron beam. Characteristic X-rays produced from the sample in response to the irradiation are spectrally dispersed and detected by a wavelength-dispersive X-ray spectrometer (WEDS). Characteristic X-ray intensities at positions where characteristic X-ray peaks are detected are measured. In this method of sample analysis, the background intensities of the characteristic X-rays at the positions where the characteristic X-ray peaks are detected are found based on a mean atomic number calculated using values derived by quantitative analysis based on characteristic X-ray intensities measured by an energy dispersive X-ray spectrometer (EDS) at the corresponding analysis positions on the sample. The background intensities are subtracted from the peak intensities at the positions where the characteristic X-ray peaks are detected by the WDS, thus finding the net characteristic X-ray intensities.

A method of analyzing a sample according to the present invention starts with irradiating the sample with an electron beam. Characteristic X-rays emanating from the sample in response to the irradiation are spectrally dispersed and detected by a wavelength-dispersive X-ray spectrometer (WDS). The background intensities of the characteristic X-rays at positions where the characteristic X-ray peaks detected in the previous step are found based on a mean atomic number calculated using values derived by quantitative analysis based on characteristic X-ray intensities measured by an energy-dispersive X-ray spectrometer (EDS) at the corresponding analysis positions on the sample. The background intensities are subtracted from the peak intensities at the characteristic X-ray peak positions detected by the WDS, thus finding the net characteristic X-ray intensities.

In the above-described method of sample analysis, the background intensities are found based on data about the background intensities relative to the mean atomic number of the sample.

An apparatus for analyzing a sample in accordance with the present invention has irradiation device for irradiating the sample with an electron beam, detection device for spectrally dispersing and detecting characteristic X-rays emanating from the sample in response to the irradiation by a wavelength-dispersive X-ray spectrometer (WDS), computing device for finding background intensities of characteristic X-rays at positions where characteristic X-ray peaks are detected by the detection device based on a mean atomic number calculated using values derived by quantitative analysis based on the characteristic X-ray intensities measured by an energy-dispersive X-ray spectrometer (EDS) at corresponding analysis positions on the sample, and computational device for finding the net characteristic X-ray intensities by subtracting background intensities from the peak intensities at the characteristic X-ray peak positions detected by the WDS.

The above-described apparatus for analyzing a sample has storage device for storing data about the background intensities at the mean atomic number of the sample. The computing device finds the background intensities based on the data.

In this way, in the present invention, background intensities at positions where the characteristic X-ray peaks spectrally dispersed by the WDS are detected are found based on a mean atomic number calculated using values derived by quantitative analysis based on the characteristic X-ray intensities measured by the EDS at the corresponding analysis positions on the sample. The background intensities are subtracted from the peak intensities at the positions where the characteristic X-ray peaks are detected by the WDS. Thus, the net characteristic X-ray intensities are found.

Consequently, the background intensities at the peak detection positions can be found without measuring either a background intensity at a background position located on a shorter wavelength side of a position where a characteristic X-ray peak spectrally dispersed by the WVDS is detected or a background intensity at a background position on a longer wavelength side. As a result, sample analysis using the WDS can be performed efficiently.

Having thus described my invention with the detail and particularity required by the Patent Laws, what is desired protected by Letters Patent is set forth in the following claims.

The invention claimed is:

1. A method of analyzing a sample by irradiating the sample with an electron beam, spectrally dispersing and detecting characteristic X-rays emanating from the sample in response to the irradiation by a wavelength-dispersive X-ray spectrometer, and measuring intensities of the characteristic X-rays at positions where characteristic X-ray peaks are detected,
   wherein background intensities of the characteristic X-rays at the positions where the characteristic X-ray peaks are detected are found based on a mean atomic number calculated using values derived by quantitative analysis based on the intensities of the characteristic X-rays measured by an energy-dispersive X-ray spectrometer at corresponding analysis positions on the sample, and
   wherein the background intensities are subtracted from the peak intensities at the positions where the characteristic X-ray peaks are detected by the wavelength-dispersive X-ray spectrometer, thus finding net characteristic X-ray intensities.

2. A method of analyzing a sample, comprising the steps of:
   irradiating the sample with an electron beam;
   spectrally dispersing and detecting characteristic X-rays emanating from the sample in response to the irradiation by a wavelength-dispersive X-ray spectrometer;
   finding background intensities of the characteristic X-rays at positions where characteristic X-ray peaks were detected in the previous detecting step based on a mean atomic number calculated using values derived by quantitative analysis based on characteristic X-ray intensities measured by an energy-dispersive X-ray spectrometer at corresponding analysis positions on the sample; and
   subtracting the background intensities from the peak intensities at the characteristic X-ray peak positions detected by the wavelength-dispersive spectrometer to thereby find net characteristic X-ray intensities.

3. A method of analyzing a sample as set forth in any one of claims 1 and 2, wherein said background intensities are found based on a table indicating the background intensities relative to the mean atomic number of the sample or on a mathematical formula.

4. An apparatus for analyzing a sample, comprising:
   irradiation means for irradiating the sample with an electron beam;
   detection means for spectrally dispersing and detecting characteristic X-rays emanating from the sample in response to the irradiation by a wavelength-dispersive spectrometer;
   computing means for finding background intensities of characteristic X-rays at positions where characteristic X-ray peaks are detected by the detection means based on a mean atomic number calculated using values derived by quantitative analysis based on the characteristic X-ray intensities measured by an energy-dispersive X-ray spectrometer at corresponding analysis positions on the sample; and
   computational means for subtracting the background intensities from the peak intensities at the characteristic X-ray peak positions detected by the wavelength-dispersive spectrometer to thereby find net characteristic X-ray intensities.

5. An apparatus for analyzing a sample as set forth in claim 4, wherein there is further provided storage means for storing data about a table indicating the background intensities relative to the mean atomic number of the sample or about a mathematical formula, and wherein said computing means finds the background intensities based on the data.

* * * * *